United States Patent

Law

[11] Patent Number: 5,230,975
[45] Date of Patent: Jul. 27, 1993

[54] PHOTOCONDUCTIVE IMAGING MEMBERS WITH UNSYMMETRICAL ALKYLALKOXY SQUARAINE COMPOSITIONS

[75] Inventor: Kock-Yee Law, Penfield, N.Y.

[73] Assignee: Xerox Corporation, Stamford, Conn.

[21] Appl. No.: 787,456

[22] Filed: Nov. 4, 1991

[51] Int. Cl.$^5$ .............................................. G03G 5/06
[52] U.S. Cl. .................................... 430/59; 430/65; 430/73; 430/126
[58] Field of Search .................... 430/59, 60, 65, 73; 430/126

[56] References Cited

U.S. PATENT DOCUMENTS

| | | | |
|---|---|---|---|
| 4,415,639 | 11/1983 | Horgan | 430/57 |
| 4,471,041 | 9/1984 | Baranyi et al. | 430/59 |
| 4,521,621 | 6/1985 | Yanus et al. | 564/307 |
| 4,624,904 | 11/1986 | Kazmaier et al. | 430/59 |
| 4,886,722 | 12/1989 | Law et al. | 430/59 |
| 5,030,537 | 7/1991 | Law et al. | 430/135 |

Primary Examiner—John Goodrow
Attorney, Agent, or Firm—E. O. Palazzo

[57] ABSTRACT

The alkoxy squaraines essentially as represented by the formula

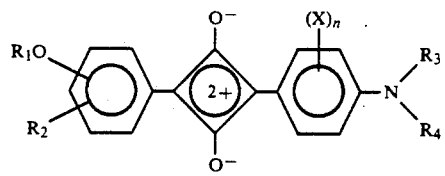

wherein $R_1$, $R_2$, $R_3$, and $R_4$ independently represent alkyl or aryl groups; X is hydrogen, halogen, alkyl, hydroxy, or alkoxy; and n is a number of from 0 to about 2.

23 Claims, 1 Drawing Sheet

PHOTOCONDUCTIVE IMAGING MEMBERS WITH UNSYMMETRICAL ALKYLALKOXY SQUARAINE COMPOSITIONS

BACKGROUND OF THE INVENTION

This invention is generally directed to squaraine compositions, and to processes for the preparation thereof. More specifically, the present invention is directed to certain alkylalkoxy unsymmetrical squaraines which can be synthesized by cycloaddition-condensation processes, thereby avoiding the use of costly squaric acid as a reactant. In one embodiment of the present invention, there are provided photoconductors with alkylalkoxy unsymmetrical squaraine compositions with improved xerographic properties inclusive of high charge acceptance, low dark decay, high photosensitivity, and improved cyclic stability when these compositions are incorporated into photoconductive imaging members. The squaraines can be prepared in embodiments of the present invention from diones as illustrated herein. Also, in an embodiment of the present invention there are provided certain alkylalkoxy unsymmetrical squaraines, imaging members thereof with the advantages indicated herein, processes for the preparation thereof, and novel squaraines. In another embodiment of the invention of the present application, there are provided imaging members with photoconductive layers comprised of the alkylalkoxy unsymmetrical squaraines illustrated herein, and charge or hole transport layers, especially those comprised of aryl amines, which members are sensitive to light in the wavelength region of from between about 400 to about 1,000, and preferably from between about 400 to 850 nanometers, enabling their use, for example, in imaging members with LED xerographic imaging apparatuses and in diode laser printers. Thus, the resulting members of the present invention in embodiments are responsive to visible light and infrared illumination originating from laser printing apparatuses wherein, for example, gallium arsenide diode lasers are selected. The photoresponsive imaging members of the present invention can also, for example, contain situated between a photogenerating layer and a hole transporting layer, or situated between a photogenerating layer and a supporting substrate with a charge transport layer in contact with the photogenerating layer, a photoconductive composition comprised of the alkylalkoxy unsymmetrical squaraines illustrated herein.

Numerous different xerographic photoconductive members, including members with photogenerating pigments of squaraines and processes thereof, are known. There are also known photoreceptor materials comprised of inorganic or organic materials wherein the charge carrier generating, and the charge carrier transport functions are accomplished by discrete contiguous layers. Additionally, layered photoreceptor materials are disclosed in the prior art, which include an overcoating layer of an electrically insulating polymeric material. Further, there are disclosed in the prior art layered photoresponsive devices including those comprised of separate generating layers, and transport layers as described in U.S. Pat. No. 4,265,990, the disclosure of which is totally incorporated herein by reference; and overcoated photoresponsive materials containing a hole injecting layer, overcoated with a hole transport layer, followed by an overcoating of a photogenerating layer; and a top coating of an insulating organic resin, reference U.S. Pat. No. 4,251,612. Examples of photogenerating layers disclosed in these patents include trigonal selenium and phthalocyanines, while examples of transport layers include certain diamines as mentioned therein. Also, there is illustrated in U.S. Pat. No. 4,415,639, the disclosure of which is totally incorporated herein by reference, the use of squaraine compositions, such as hydroxy squaraines, as a photoconductive layer in an infrared sensitive photoresponsive device. More specifically, there is described in this patent an improved photoresponsive device containing a substrate, a hole blocking layer, an optional adhesive interfacial layer, an inorganic photogenerating layer, a photoconductive composition capable of enhancing or reducing the intrinsic properties of the photogenerating layer, which photoconductive composition is selected from various squaraine compositions, including hydroxy squaraine compositions, and a hole transport layer. Other patents disclosing photoconductors with squaraines are U.S. Pat. Nos. 4,471,041; 4,486,520; 4,508,803; 4,507,480; 4,552,822; 4,390,610; 4,353,971; 4,391,888; 4,607,124 and 4,746,756. In the '124 patent, the disclosure of which is totally incorporated herein by reference, there are illustrated processes for the preparation of a squaraine mixture, one of which may be a fluorinated component, see column 5, wherein the known squaric acid reaction is accomplished in the presence of a fluoroaniline, and the use thereof in photoconductive imaging members. The '756 patent, the disclosure of which is totally incorporated herein by reference, illustrates layered imaging members with certain fluorinated squaraines, wherein $R_2$ and $R_3$ may be a heterocyclic, such as 2-pyrolyl, see columns 3, 4, 5 and 6, for example.

Furthermore, there are illustrated in U.S. Pat. No. 4,624,904, the disclosure of which is totally incorporated herein by reference, photoconductive imaging members with unsymmetrical hydroxy squaraine compositions, and aryl amine hole transport layers. The aforementioned unsymmetrical squaraine compounds can be prepared, for example, by the initial preparation of an aryl cyclobutenedione intermediate, followed by the reaction thereof with a substituted aniline. More specifically, with respect to method A illustrated in the '904 patent, the aryl cyclobutenedione is prepared by heating with reflux at a temperature of from about 40° to about 50° C., depending on the solvent selected; about 20 millimoles to about 50 millimoles of substituted aniline; from about 60 millimoles to about 150 millimoles of dihalocyclobutenedione; and from about 100 milliliters to about 1,000 milliliters of a Friedel-Crafts solvent inclusive of, for example, carbon disulfide, nitrobenzene or methylene chloride. This reaction is accomplished in the presence of from about 200 to about 900 millimoles of a catalyst, such as aluminum chloride, and the resulting substituted aniline is reacted with a hydroxy substituted aniline in the presence of an aliphatic alcoholic solvent. Subsequent to separation, there are obtained the desired unsymmetrical squaraine compounds of the formula as detailed on page 8, beginning at line 10, for example. Also, in U.S. Pat. No. 4,521,621, there are described photoresponsive imaging members, or photoconductors containing unsymmetrical squaraines, reference for example the formula in column 7, line 60, by forming a mixture of squaric acid, a primary alcohol, a first tertiary amine, and a second tertiary amine.

In U.S. Pat. No. 4,524,220, the disclosure of which is totally incorporated herein by reference, there is illustrated a squaraine process by the reaction of squaric acid and an aromatic aniline in the presence of an aliphatic amine. Also, in U.S. Pat. No. 4,524,219 there is described a process for the preparation of squaraines by the reaction of an alkyl squarate and an aniline in the presence of an aliphatic alcohol, and an optional acid catalyst. Moreover, disclosed in U.S. Pat. No. 4,524,218 are processes for the preparation of squaraines by the reaction of squaric acid with an aromatic amine, and a composition selected from the group consisting of phenols, and phenol squaraines, which reaction is accomplished in the presence of an aliphatic alcohol, and an optional azeotropic catalyst. Other processes for preparing squaraines are illustrated in U.S. Pat. No. 4,525,592, wherein there is described the reaction of a dialkyl squarate, and an aniline in the presence of an aliphatic alcohol and an acid catalyst; and U.S. Pat. No. 4,746,756 mentioned herein wherein the fluorinated squaraines disclosed are prepared by the reaction of an aromatic fluorinated amine and squaric acid in the presence of an aliphatic alcohol and an optional azeotropic cosolvent. The aforementioned squaraines can be selected as photogenerating pigments for layered photoconductors.

In U.S. Pat. No. 4,886,722, the disclosure of which is totally incorporated herein by reference, there is illustrated the provision of certain unsymmetrical squaraine compositions and processes for the preparation thereof. More specifically, there are disclosed in the '722 patent photoconductive imaging members containing as photoconductive compositions unsymmetrical noncyclized squaraines of the following formula

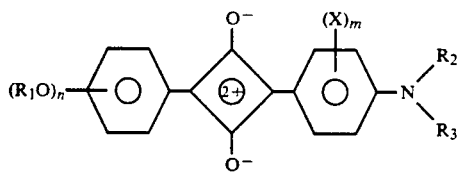

wherein $R_1$, $R_2$ and $R_3$ are independently selected from alkyl groups or aryl groups; X is hydroxy, hydrogen, alkyl, alkoxy, or halo; n is a number of from 1 to about 3; and m is a number of from 0 to about 2. Preferred halogens include fluorine and chlorine. Examples of alkyl groups include those containing from about 1 to about 25 carbon atoms such as methyl, ethyl, propyl, butyl, pentyl, hexyl, heptyl, dodecyl and the like; while examples of aryl groups include those with from about 6 to about 24 carbon atoms including substituted aryl groups such as phenyl and benzyl. Alkoxy groups are represented by those containing from about 1 to about 10 carbon atoms such as methoxy, propoxy, butoxy, pentoxy, heptoxy, and the like, inclusive in some situations of aryl alkoxy substituents such as phenyl alkoxy. Halo includes fluoride, bromide, chloride and iodide Specific examples of unsymmetrical squaraines illustrated in the '722 patent include 4-dimethylaminophenyl-4'-methoxyphenyl squaraine; 2-hydroxy-4-dimethylaminophenyl-4'-methoxyphenyl squaraine; 2-methyl-4-dimethylaminophenyl-4'-methoxyphenyl squaraine; 2-fluoro-4-dimethylaminophenyl-4'-methoxyphenyl squaraine; 2-methoxy-4-dimethylaminophenyl-4'-methoxyphenyl squaraine; 4-benzylmethylaminophenyl-4'-methoxyphenyl squaraine; 4-dimethylaminophenyl-3',4'-dimethoxyphenyl squaraine; 2-hydroxy-4-dimethylaminophenyl-3',4'-dimethoxyphenyl squaraine; 2-methyl-4-dimethylaminophenyl-3',4'-dimethoxyphenyl squaraine; 2-fluoro-4-dimethylaminophenyl-3',4'-dimethoxyphenyl squaraine; 2-methoxy-4-dimethylaminophenyl-3',4'-dimethoxyphenyl squaraine; 4-dimethylaminophenyl-3',4',5'-trimethoxyphenyl squaraine; 2-hydroxy-4-dimethylaminophenyl-3',4',5'-trimethoxyphenyl squaraine; 2-chloro-4-dimethylaminophenyl-4-methoxyphenyl squaraine; 2-chloro-4-dimethylaminophenyl-3',4'-dimethoxyphenyl squaraine; 4-diethylaminophenyl-4'-methoxyphenyl squaraine; and 4-diethylaminophenyl-3',4'-dimethoxyphenyl squaraine. With the squaraines of the present invention, an alkyl and alkoxy group are present on the same phenyl substituent as contrasted to the aforementioned squaraines. In embodiments, the photosensitivity of the layered imaging members with the squaraines illustrated herein can decrease sharply beyond 800 nanometers, which can be an advantage in improving the cyclic stability thereof in various imaging apparatuses.

The squaraine compositions of the '722 patent are generally prepared by a cycloaddition-condensation reaction. More specifically, these squaraines can be prepared by condensing, for example, a 1-alkoxyaryl-2-hydroxycyclobutene-3,4-dione derivative with an N,N-dialkylaniline derivative, such as 1-3',4'-dimethoxyphenyl-2-hydroxycyclobutene-3,4-dione or 3-fluoro-N,N-dimethylaniline in a molar ratio of about 1 to 6, and preferably in a ratio of about 1 to 3 in the presence of an aliphatic alcohol, such as propanol, and an optional drying reagent. About 500 milliliters of alcohol per 0.1 mole of 1-alkoxyaryl-2-hydroxycyclobutene-3,4-dione are selected, however, up to about 1,000 milliliters of alcohol to about 0.5 to 1 mole of 1-alkoxyaryl-2-hydroxycyclobutene-3,4-dione can be selected. The drying reagent can be heterogeneous, such as molecular sieves, or homogeneous, such as a trialkyl orthoformate. A ratio of 1 to 10 equivalents of drying reagent, more specifically tributyl orthoformate, can be used with a ratio of about 1 to 4 to the cyclobutene dione being preferred. Also, the reaction is generally accomplished at a temperature of about 60° C. to about 130° C., and preferably at a temperature of 70° C. to about 100° C. with stirring until the reaction is completed. Subsequently, the desired product can be isolated from the reaction mixture by known techniques such as filtration, and the product is identified by analytical tools including IR, NMR, and mass spectrometry. Further, carbon, hydrogen, fluorine, and nitrogen elemental analysis can be selected for aiding the identification of the product.

The 1-alkoxyaryl-2-hydroxycyclobutene-3,4-dione reactant can be prepared as indicated in the literature, and specifically by a known [2+2] cycloaddition process involving a tetraalkoxy olefin and an alkoxyarylketene generated in situ by the reaction of an alkoxyarylacetyl chloride and a base. Thus, for example, 3,4-dimethoxyphenylacetyl chloride can be reacted with tetraethoxyethylene in n-hexane in the presence of triethylamine. The ratio of acid chloride to tetraethoxyethylene is about 1 to 10 with 1 to 4 being preferred. The amount of triethylamine used will vary, however, usually an amount equivalent to the amount of the acid chloride is selected, and the reaction mixture is stirred at room temperature until the reaction is complete. Also, the [2+2] cyclo adduct product mixture can be hydrolyzed directly by refluxing in an aqueous hydrochloric acid solution or pre-purified by stirring with silica gel or alumina in a solvent, such as n-hexane or ether, before the hydrolysis. The hydrolyzed product is then purified by conventional technique such as recrystallization. This results in reactants such as 1-4′-methoxyphenyl-2-hydroxycyclobutene-3,4-dione, 1-3′,4′-dimethoxyphenyl-2-hydroxycyclobutene-3,4-dione, and 1-3′,4′,5′-trimethoxyphenyl-2-hydroxycyclobutene-3,4-dione, which can then be reacted with a N,N-dialkylaniline enabling the formation of the unsymmetrical squaraines.

The squaraines of the aforementioned '722 patent can be incorporated into various photoconductive imaging members. One such member is comprised of a supporting substrate, a hole transport layer and as a photoconductive layer situated between the supporting substrate, and the hole transport layer the squaraines. In another embodiment of the copending application, there is envisioned a layered photoresponsive device comprised of a supporting substrate, a certain squaraine photoconductive layer and situated between the supporting substrate and the photoconductive layer, a hole transport layer. In one specific illustrative embodiment of the copending application, the photoresponsive device can be comprised of (1) a supporting substrate, (2) a hole blocking layer, (3) an optional adhesive interface layer, (4) an unsymmetrical squaraine photogenerating layer, and (5) a hole transport layer. Thus, a specific photoresponsive device of the copending application can be comprised of a conductive supporting substrate, a hole blocking metal oxide layer in contact therewith, an adhesive layer, an unsymmetrical squaraine photogenerating material overcoated on the optional adhesive layer, and as a top layer, a hole transport layer comprised of certain diamines dispersed in a resinous matrix. The photoconductive layer composition, when in contact with the hole transport layer, is capable of allowing holes generated by the photogenerating layer to be transported. Examples of aryl amine hole transport molecules that may be selected for the photoconductor devices are illustrated in U.S. Pat. No. 4,265,990, the disclosure of which is totally incorporated herein by reference.

The photoresponsive devices described in the '722 patent and the imaging members of the present invention can be utilized in various imaging systems including xerographic imaging processes. Additionally, the imaging members of the present invention can be selected for imaging and printing systems with visible light and/or infrared light. In this embodiment, the photoresponsive devices may be negatively charged, exposed to light in a wavelength of from about 400 to about 850 nanometers, either sequentially or simultaneously, followed by developing the resulting image and transferring to paper. The above sequence may be repeated many times.

The following prior art is also mentioned: U.S. Pat. Nos. 4,521,621; 4,607,124 and 4,746,756, mentioned hereinbefore, of which the '756 patent illustrates fluorinated squaraines wherein $R_1$, $R_2$ and $R_3$ may be a heterocyclic, see column 5, lines 4 to 29, for example. Further, in Angew Chem. Int. Ed. Engl 5, 894 (1966), H. E. Spenger and W. Ziegenbein there is illustrated the preparation of squaraines by condensing one equivalent of squaric acid and two equivalents of aniline derivatives under azeotropic conditions; many squaraines have been prepared by the aforementioned processes, reference for example U.S. Pat. Nos. 3,617,270; 3,824,099; 4,175,956; 4,486,520 and 4,508,803; and hydroxy and certain fluorinated squaraines for xerographic photoreceptor applications, reference K. Y. Law and F. C. Bailey, *J. Imaging Science*, 31, 172 (1987).

In U.S. Pat. No. 5,077,160 (D/89407), the disclosure of which is totally incorporated herein by reference, there are illustrated photoconductive imaging members with photoconductive fluorinated squaraine compositions of the formulas indicated including bis(2-fluoro-4-N-pyrrolidinophenyl) squaraine; 2-fluoro-4-N-pyrrolidinophenyl-4′-dimethylaminophenyl squaraine; 2-fluoro-4-N-pyrrolidinophenyl-2′-hydroxy-4′-dimethylaminophenyl squaraine; 2-fluoro-4-N-pyrrolidinophenyl-2′-methyl-4′-dimethylaminophenyl squaraine; 2-fluoro-4-N-pyrrolidinophenyl-4′-dimethylaminophenyl squaraine; 2-fluoro-4-N-pyrrolidinophenyl-4′-methoxyphenyl squaraine; 2-fluoro-4-N-pyrrolidinophenyl-3′,4′-dimethoxyphenyl squaraine; 2-fluoro-4-N-pyrrolidinophenyl-3′,4′,5′-trimethoxyphenyl squaraine; 2-fluoro-4-N-pyrrolidinophenyl-2′-methoxy-4′-dimethylaminophenyl squaraine; 2-fluoro-4-N-pyrrolidinophenyl-4′-methylbenzylaminophenyl squaraine; 2-fluoro-4-N-pyrrolidinophenyl-2′-chloro-4′-dimethylaminophenyl squaraine; 2-fluoro-4-N-pyrrolidinophenyl-9′-julolidinyl squaraine; 2-fluoro-4-N-pyrrolidinophenyl-8′-hydroxy-9′-julolidinyl squaraine; and 2-fluoro-4-N-pyrrolidinophenyl-8′-fluoro-9′-julolidinyl squaraine.

U.S. Pat. No. 5,106,713 (D/90086), the disclosure of which is totally incorporated herein by reference, there are illustrated photoconductive imaging members with photoconductive cyclized unsymmetrical squaraine compositions represented by the following Formula as illustrated in the '713 patent:

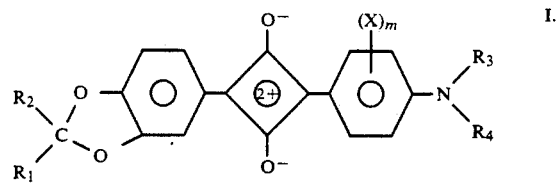

wherein $R_1$ and $R_2$ are independently selected from alkyl and hydrogen; $R_3$ and $R_4$ are independently selected from alkyl and benzyl; X is hydrogen, hydroxy, alkyl, alkoxy or halogen; and m is a number of from zero to about 3. Illustrative examples of specific squaraines disclosed in the aforementioned copending application include 3,4-methylenedioxyphenyl-4′-dimethylaminophenyl squaraine; 3,4-methylenedioxyphenyl-2′-fluoro-4′-dimethylaminophenyl squaraine; 3,4-methylenedioxyphenyl-2′-hydroxy-4′-dimethylaminophenyl squaraine; 3,4-methylenedioxyphenyl-2′-methyl-4′-dimethylaminophenyl squaraine; 3,4-methylenedioxyphenyl-2′-methoxy-4′-dimethylaminophenyl squaraine; 3,4-methylenedioxphenyl-2′-chloro-4′-dimethylaminophenyl squaraine; 3,4-methylenedioxyphenyl-2′,6,′-difluoro-4′-dimethylaminophenyl squaraine; 3,4-methylenedioxyphenyl-4′-N-pyrrolidinophenyl squaraine; 3,4-methylenedioxyphenyl-2′-fluoro-4′-pyrrolidinophenyl squaraine; 3,4-methylenedioxyphenyl-8′-fluoro-9′-julolidinyl squaraine; 3,4-methylenedioxyphenyl-2′-hydroxy-4′-N-pyrrolidinophenyl squaraine; 3,4-methylenedioxyphenyl-2′-fluoro-4′-methylbenzyl aminophenyl squaraine; and the like.

Although the above squaraines and processes thereof are suitable for their intended purposes, there continues to be a need for other photoconductive squaraines. Additionally, and more specifically there remains a need for simple, economical processes for preparing certain squaraine compositions with stable properties, which when incorporated into photoconductive devices can result in reduced dark decay characteristics, and increased charge acceptance values as compared to many similar squaraine compositions. In addition, there remains a need for photoconductive imaging members with certain stable electrical characteristics, that is for example the aforementioned imaging members are electrically stable for over 100,000 xerographic imaging cycles in embodiments thereof. In addition, imaging members with the squaraines of the present invention in embodiments thereof are sensitive to a broad range of wavelengths, including visible and infrared light, such as of from about 400 to about 850 nanometers, enabling such members to be useful in electrophotographic imaging and printing processes, including processes wherein diode lasers, or LED (light emitted diodes) image bars are selected.

SUMMARY OF THE INVENTION

It is therefore a feature of the present invention to provide certain squaraine compositions and processes for the preparation thereof.

Another feature of the present invention is to provide certain alkylalkoxy unsymmetrical squaraine compositions and imaging members comprised of these squaraines, which members are sensitive to wavelengths of from about 400 to about 1,000 and preferably from about 400 to about 850 nanometers.

In another feature of the present invention there are provided improved processes for preparing alkylalkoxy squaraine compositions from alkylalkoxyarylhydroxycyclobutenediones, and photoresponsive imaging members thereof which can possess excellent dark decay properties, high charge acceptance values, and electrical stability.

In yet another feature of the present invention there are provided simple, economical processes for preparing alkylalkoxy unsymmetrical squaraines, which can be selected for layered photoconductive imaging members containing aryl amine hole transport layers.

A further feature of the present invention resides in improved processes for obtaining alkylalkoxy unsymmetrical squaraine compositions of excellent sensitivity, and excellent cyclic stability when incorporated into layered imaging members with hole transport molecules.

Further, in another feature of the present invention there are provided photoconductive imaging members with alkoxy, with from 1 to about 10 carbon atoms, unsymmetrical squaraines, which members can be simultaneously responsive to infrared light and to visible light.

Additionally, another feature of the present invention resides in the provision of imaging and printing methods with the photoconductive imaging members illustrated herein.

These and other features of the present invention in embodiments thereof can be accomplished by the provision of squaraine compositions, and processes for the preparation thereof. More specifically, the present invention is directed to photoconductive imaging members with photoconductive alkylalkoxy unsymmetrical squaraine comositions represented by the following Formula I

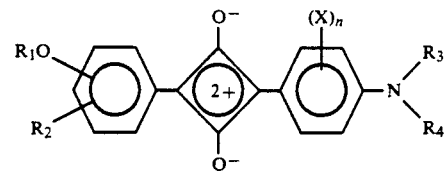

wherein $R_1$, $R_2$, $R_3$, and $R_4$ independently represent alkyl or aryl groups of, for example, from 1 to about 25, and preferably 6 carbon atoms; X is hydrogen, halogen, such as fluoride, or chloride, alkyl, hydroxy, alkoxy with, for example, from 1 to about 25 carbon atoms and n is a number of from 0 to about 2, and more specifically n is the number 0, 1, or 2.

Examples of alkyl and alkoxy groups include those containing from about 1 to about 25, and preferably from 1 to about 10 carbon atoms such as methyl, ethyl, propyl, butyl, pentyl, pentoxy, hexyl, hexoxy, heptyl, heptoxy, octyl, nonyl, dodecyl and the like; while examples of aryl groups include those with from about 6 to about 24 carbon atoms including substituted aryl groups, such as phenyl, naphthyl and benzyl. Typical alkoxy groups contain from about 1 to about 25, and preferably from 1 to about 10 carbon atoms, such as methoxy, propoxy, butoxy, pentoxy, heptoxy, and the like, inclusive in some situations of aryl alkoxy substituents, such as phenoxy. Halo includes, for example, fluoride and chloride.

Illustrative examples of specific squaraines of the present invention include 3-methyl-4-methoxyphenyl-2'-fluoro-4'-dimethylaminophenyl squaraine; 3-methyl-4-methoxyphenyl-4'-dimethylaminophenyl squaraine; 3-methyl-4-methoxyphenyl-2'-methyl-4'-dimethylaminophenyl squaraine; 3-methyl-4-methoxyphenyl-2'-hydroxy-4'-dimethylaminophenyl squaraine; 3-methyl-4-methoxyphenyl-2'-methoxy-4'-dimethylaminophenyl squaraine; 3-methyl-4-methoxyphenyl-2'-chloro-4'-dimethylaminophenyl squaraine; 3-methyl-4-methoxyphenyl-2',6'-difluoro-4'-dimethylaminophenyl squaraine; 3-methyl-4-methoxyphenyl-2-fluoro-4'-N-pyrrolidinophenyl squaraine; 3-methyl-4-methoxyphenyl-2'-fluoro-4'-benzylmethylaminophenyl squaraine; and 3-methyl-4-methoxyphenyl-8'-fluoro-9'-julolidinyl squaraine. Formulas for a number of the squarines are as follows:

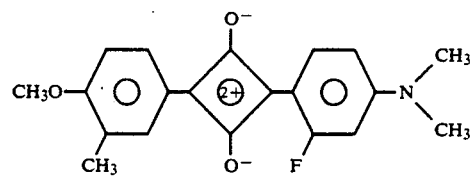

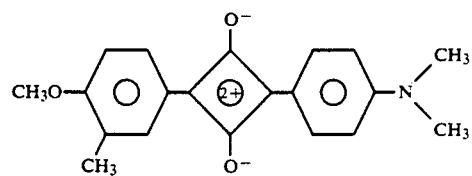

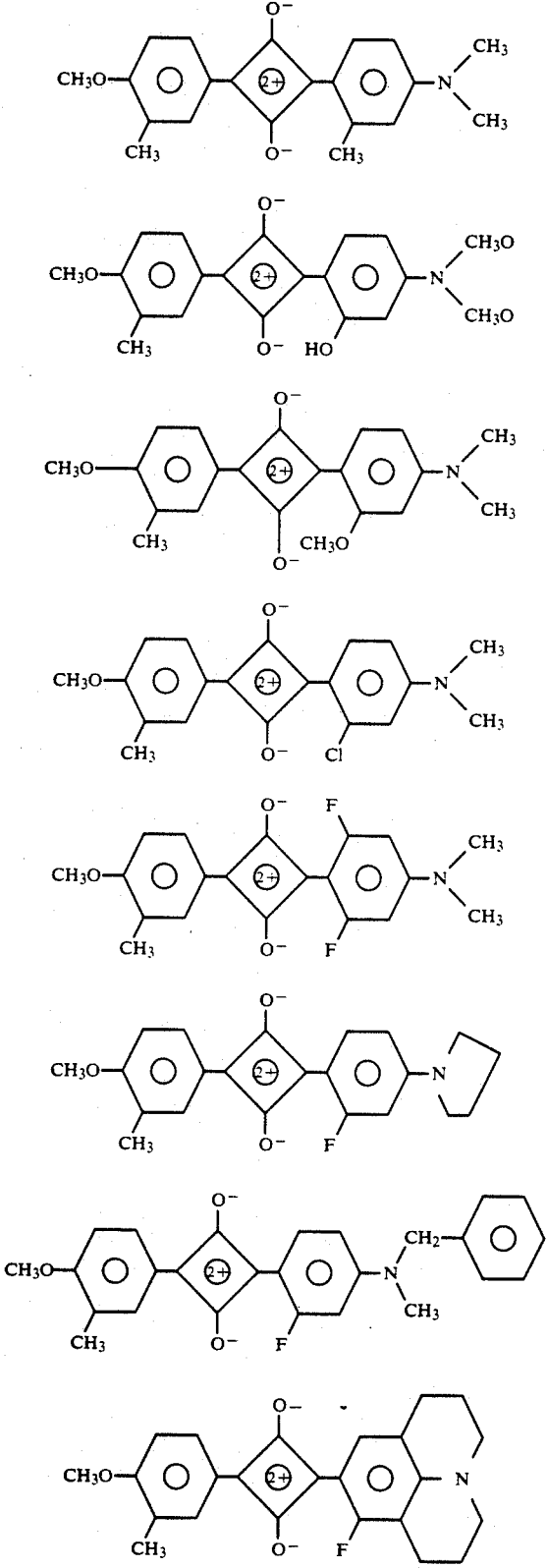

The squaraines of the present invention can be prepared from a precursor dione illustrated in U.S. Pat. No. 5,106,713 (D/90086), and similar to the processes as illustrated in U.S. Pat. Nos. 4,886,722 and 4,922,018, the disclosures of which are totally incorporated herein by reference. In one embodiment, the process comprises initially preparing the corresponding halide, such as the chloride, by the reaction of 3-methyl-4-methoxyphenylacetic acid with thionyl halide, such as thionyl chloride, with heating to result in 3-methyl-4-methoxyphenylacetyl chloride. The aforementioned chloride can then be reacted with tetraethoxyethylene, followed by hydrolysis of the product after heating enabling the product precursor 1-(3'-methyl-4'-methoxyphenyl)-2-hydroxycyclobutene-3,4-dione. Subsequently, the resulting aforementioned dione after separation can be reacted with an aniline, such as a fluoro-N,N-dimethylaniline, in alcohol, such as propanol, and an orthoformate, such as tributyl orthoformate, to enable the squaraine 3-methyl-4-methoxyphenyl-2'-fluoro-4'-dimethylaminophenyl squaraine.

In embodiments thereof, the squaraine compositions of the present invention are generally prepared by a cycloaddition-condensation reaction. More specifically, the squaraines can be prepared by condensing, for example, a 1-alkylalkoxyaryl-2-hydroxycyclobutene-3,4-dione derivative with an N,N-dialkylaniline derivative, such as 1-3'-methyl-4'-methoxyphenyl-2-hydroxycyclobutene-3,4-dione and 3-fluoro-N,N-dimethylaniline in a molar ratio of about 1 to 6, and preferably in a ratio of about 1 to 3 in the presence of an aliphatic alcohol with, for example, from 1 to about 10 carbon atoms, such as propanol, and an optional drying reagent. About 500 milliliters of alcohol per 0.1 moles of 1-alkylalkoxyaryl-2-hydroxycyclobutene-3,4-dione can be selected, however, in embodiments up to about 1,000 milliliters of alcohol to about 0.5 to 1 moles of 1-alkylalkoxyaryl-2-hydroxycyclobutene-3,4-dione can be selected. The drying reagent can be heterogeneous such as molecular sieves, or homogeneous such as a trialkyl orthoformate. A ratio of about 1 to 10 equivalents of drying reagent, such as tributyl orthoformate, can be used with a ratio of about 1 to 4 to the cyclobutene dione being preferred. Also, the reaction can generally be accomplished at a temperature of about 60° C. to about 130° C., and preferably at a temperature of 70° C. to about 100° C. with stirring until the reaction is completed. Subsequently, the desired product can be isolated from the reaction mixture by known techniques such as filtration, and the product can be identified by analytical tools including IR, NMR, and mass spectrometry. Further, carbon, hydrogen, fluorine, nitrogen and oxygen elemental analysis can be selected for aiding the identification of the product.

The 1-alkylalkoxyaryl-2-hydroxycyclobutene-3,4-dione reactant can be prepared as indicated in the literature referred to herein, and specifically by a known [2+2] cycloaddition process involving a tetraalkoxy olefin and an alkylalkoxyarylketene generated in situ by the reaction of an alkylalkoxyarylacetyl chloride and a base. Thus, for example, 3-methyl-4-methoxyphenylacetyl chloride can be reacted with tetraethoxyethylene in n-hexane in the presence of triethylamine. The ratio of acid chloride to tetraethoxyethylene is about 1 to 10 with 1 to 4 being preferred. The amount of triethylamine used will vary, however, usually an amount equivalent to the amount of the acid chloride is selected, and the reaction mixture is stirred at room temperature until the reaction is complete. Also, the [2+2] cyclo adduct product mixture can be hydrolyzed directly by refluxing in an aqueous hydrochloric acid solution or prepurified by stirring with silica gel or alumina in a solvent, such as n-hexane or ether, before the hydrolysis. The hydrolyzed product is then purified by conventional technique such as recrystallization. This results in reactants such as 1-(3'-methyl-4'methoxyphenyl)-2-hydroxycyclobutene-3,4-dione, which can be reacted with a N,N-dialkylaniline as indicated herein thus enabling the formation of the unsymmetrical squaraines of the present invention in embodiments thereof.

In an embodiment, the precursor dione can be represented by the following formula:

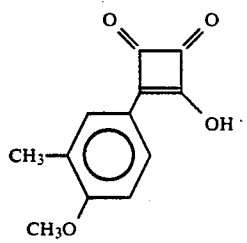

The squaraine compounds of the present invention can be incorporated into various photoconductive imaging members. One such member is comprised of a supporting substrate, a hole transport layer, and as a photoconductive layer situated between the supporting substrate and the hole transport layer the alkylalkoxy squaraine of the present invention. In another embodiment, there is envisioned a layered photoresponsive device, or photoconductor comprised of a supporting substrate, a photoconductive layer comprised of the alkylalkoxy squaraine compound of the present invention, and situated between the supporting substrate and the photoconductive layer a hole transport layer. In one specific illustrative embodiment, the photoresponsive device can be comprised of (1) a supporting substrate, (2) a hole blocking layer, (3) an optional adhesive interface layer, (4) an alkylalkoxy unsymmetrical squaraine photogenerating layer, and (5) a hole transport layer. Thus, a specific photoconductor of the present invention can be comprised of a conductive supporting substrate, a hole blocking metal oxide layer in contact therewith, an adhesive layer, an alkylalkoxy unsymmetrical squaraine photogenerating material overcoated on the optional adhesive layer, and as a top layer, a hole transport layer comprised of known components diamines dispersed in a resinous matrix. The photoconductive layer composition, when in contact with the hole transport layer, is capable of allowing holes generated by the photogenerating layer to be transported. Examples of aryl amine hole transport molecules that may be selected for the photoconductor devices are illustrated in U.S. Pat. No. 4,265,990, the disclosure of which is totally incorporated herein by reference. Also, examples of charge transport molecules are illustrated in U.S. Pat. No. 4,921,773, and the patents mentioned therein, the disclosures of each of the aforementioned patents, including the '773 patent, being totally incorporated herein by reference.

The photoresponsive devices described herein can be incorporated into various imaging systems such as those conventionally known as xerographic imaging processes. Additionally, the imaging members of the present invention can be selected for imaging and printing systems with visible light and/or infrared light. In this embodiment, the photoresponsive devices may be negatively charged, exposed to light in a wavelength of from about 400 to about 850 nanometers, either sequentially or simultaneously, followed by developing the resulting image and transferring to paper. The above sequence may be repeated numerous times, such as for from between about 50,000 to about 100,000.

BRIEF DESCRIPTION OF THE DRAWINGS

For a further understanding of the features of the present invention, the following description of various embodiments thereof is provided wherein.

DESCRIPTION OF SPECIFIC EMBODIMENTS

Specific embodiments of the present invention will now be illustrated, it being noted that substantially equivalent imaging members are also embraced within the scope of the present invention.

Figure 1:
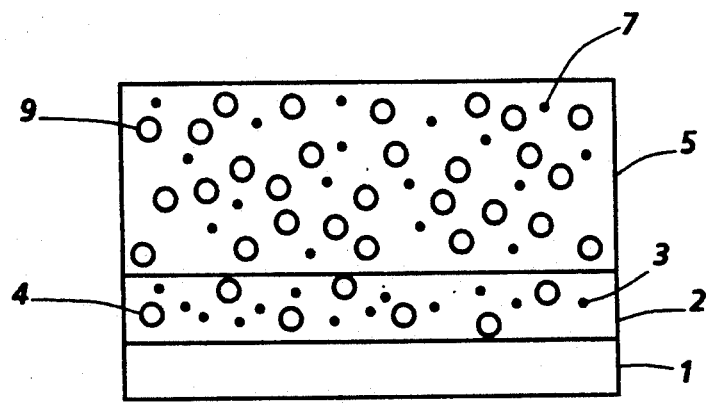
FIGS. 1, 2, and 3 are partially schematic views of examples of photoconductive imaging members of the present invention.

FIG. 1 illustrates a photoconductive imaging member of the present invention comprising a supporting substrate 1, a photogenerating layer 2 comprising the squaraines 3 illustrated herein optionally dispersed in a resinous binder composition 4, and a charge carrier transport layer 5, which comprises transporting molecules 7 dispersed in an inactive resinous binder composition 9.

Figure 2:
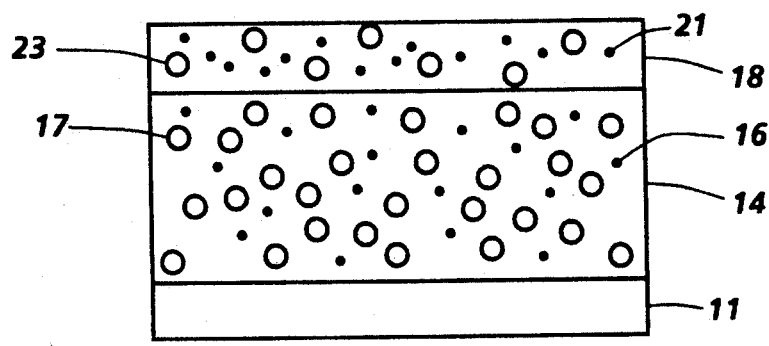

FIG. 2 illustrates the same member as that shown in FIG. 1 with the exception that the hole transport layer is situated between the supporting substrate and the photogenerating layer. More specifically, this Figure illustrates a photoconductive imaging member comprising a supporting substrate 11, a hole transport layer 14 comprising aryl amine hole transport molecules 16 dispersed in an inactive resinous binder composition 17, and a photogenerating layer 18 comprising a squaraine 21 of the formula as illustrated herein, especially 3-methyl-4-methoxyphenyl-2'-fluoro-4'-dimethylaminophenyl squaraine optionally dispersed in a resinous binder composition 23.

Figure 3:
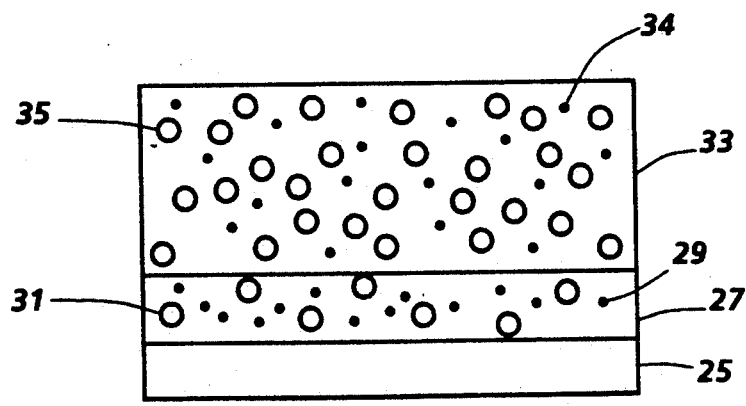

FIG. 3 illustrates a photoconductive imaging member of the present invention comprising a supporting substrate 25, a photogenerating layer 27 comprising the squaraine 29, 3-methyl-4-methoxyphenyl-2'-fluoro-4'-dimethylaminophenyl squaraine dispersed in a resinous binder composition 31, and a charge carrier hole transport layer 33, which comprises hole transporting molecules 34 dispersed in an inactive resinous binder composition 35.

The supporting substrate of the imaging members may comprise known insulating materials such as an inorganic or organic polymeric materials, including MYLAR ®, a commercially available polymer; a layer of an organic or inorganic material having a semiconductive surface layer such as indium tin oxide or aluminum arranged thereon; or a conductive material such as aluminum, titanium, chromium, nickel, brass, or the like. The substrate may be flexible, seamless, or rigid and may have a number of different configurations, such as a plate, a cylindrical drum, a scroll, an endless flexible belt, and the like. Preferably, the substrate is in the form of an endless flexible belt. In some situations, it may be desirable to coat an anticurl layer, such as polycarbonate materials commercially available as MAK-ROLON ®, on the back of the substrate, particularly when the substrate is an organic polymeric material. Other known substrates may be selected.

The thickness of the substrate layer depends on a number of factors, including economic considerations, the components of the other layers, and the like. Thus, this layer may be of substantial thickness, for example over 100 mils, or of minimal thickness provided that there are no adverse effects on the system. In a preferred embodiment, the thickness of this layer is from about 2 mils to about 20 mils.

Generally, the squaraine photogenerating layer has a thickness of from about 0.05 micron to about 10 microns or more, and preferably has a thickness of from about 0.1 micron to about 5 microns. The thickness of this layer, however, is dependent primarily upon the photogenerating weight loading, which may vary from about 5 to about 100 percent, the components of the other layers, and the like. Generally, it is desirable to provide this layer in a thickness sufficient to absorb a substantial amount, for example about 85 percent or more, of the incident radiation which is directed upon it in the imagewise or printing exposure step. The maximum thickness of this layer is dependent primarily upon factors such as mechanical considerations, such as the specific squaraine compound selected, the thicknesses of the other layers, and whether a flexible photoconductive imaging member is desired. Optionally, resin binders for the photogeneration layer include poly(vinyl acetal) such as polyvinyl formal, polyvinylbutyral and the like.

The charge transport layer can be comprised of various components providing, for example, that they effectively transport charges (holes) such as an aryl amine compound dispersed in a resinous binder and other components, reference the '773 patent mentioned herein, the disclosure of which is totally incorporated herein by reference. In one embodiment, the charge transport layers are comprised of aryl amine compounds of the formula:

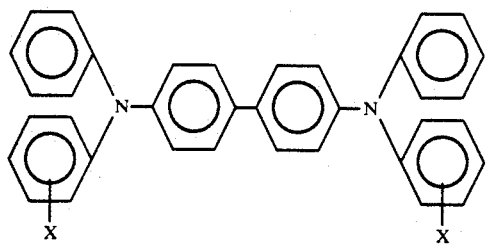

wherein X is selected from the group consisting of alkyl and halogen. Preferably, X is selected from the group consisting of methyl and chloride in either the ortho, meta, or para positions. Suitable inactive binder materials for the hole transport layer include known highly insulating resins, which generally have a resistivity of at least $10^{12}$ ohm-cm to prevent undue dark decay. Compounds corresponding to the above formula include N,N'-diphenyl-N,N'-bis(alkylphenyl)-[1,1'-biphenyl]-4,4'-diamine, wherein alkyl is selected from the group consisting of methyl, such as 2-methyl, 3-methyl and 4-methyl, ethyl, propyl, butyl, hexyl, and the like. With halo substitution, the amine is N,N'-diphenyl-N,N'-bis(-halo phenyl)-[1,1'-biphenyl]-4,4'-diamine, wherein halo is 2-chloro, 3-chloro or 4-chloro. Other electrically active small molecules that can be dispersed in the electrically inactive resin to form a layer which will transport holes include bis(4-diethylamino-2-methylphenyl)-phenyl methane, 4',4''-bis(diethylamino)-2',2''-dimethyltriphenyl methane, bis-4-(diethylaminophenyl)phenyl methane, and 4,4'-bis(diethylamino)-2,2'-dimethyltriphenyl methane. Generally, the hole transport layer has a thickness of from about 5 to about 75 microns, and preferably of from about 10 to about 40 microns.

Examples of highly insulating and transparent resinous components or inactive binder resinous material for the transport layer include materials such as those described in U.S. Pat. No. 3,121,006, the disclosure of which is totally incorporated herein by reference. Specific examples of suitable organic resinous materials include polycarbonates, acrylate polymers, vinyl polymers, cellulose polymers, polyesters, polysiloxanes, polyamides, polyurethanes and epoxies as well as block, random or alternating copolymers thereof. Preferred electrically inactive binder materials are polycarbonate resins having a molecular weight of from about 20,000 to about 100,000 with a molecular weight in the range of from about 50,000 to about 100,000 being particularly preferred. The materials most preferred as electrically inactive resinous materials are poly(4,4'-dipropylidine-diphenyline carbonate) with a weight average molecular weight of from about 35,000 to about 40,000 available as LEXAN 145 ® from General Electric Company; poly(4,4'-isopropylidine-diphenyline carbonate) with a weight average molecular weight of from about 40,000 to about 45,000 available as LEXAN 141 ® from General Electric Company; a polycarbonate resin having a weight average molecular weight of from about 50,000 to about 100,000 available as MAKROLON ® from Farbenfabricken Bayer AG; and a polycarbonate having a weight average molecular weight of from about 20,000 to about 50,000 available as MERLON ® from Mobay Chemical Company; polyoxycarbonyloxy-1,4-phenylenecyclohexylidene-1,4-phenylene with a weight average molecular weight of about 23,000, available from Mitsubishi Kasei Corporation as PC(Z). Generally, the resinous binder contains from about 10 to about 75 percent by weight of the active material corresponding to the foregoing formula, and preferably from about 35 percent to about 50 percent of this material. Examples of binder material for the squaraine photogenerating layer are poly(vinyl acetals), polycarbonates as mentioned herein, polyesters, polyvinyl carbazole, and the like. Typical effective amounts of binder can be selected including, for example, from about 5 to about 95, and preferably from about 10 to about 70 weight percent, in embodiments of the present invention, and providing that squaraine enables photogeneration.

The photoconductive imaging member may optionally contain a hole blocking layer situated between the supporting substrate and the photogenerating layer. This layer may comprise metal oxides, such as aluminum oxide and the like, or materials such as silanes. The primary purpose of this layer is to prevent hole injection from the substrate during and after charging. Typically, this layer is of a thickness of less than 50 Angstrons, although it may be as thick as 500 Angstroms in some instances.

In addition, the photoconductive imaging member may also optionally contain an adhesive interface layer situated between the hole blocking layer and the photogenerating layer. This layer may comprise a polymeric material such as polyester, polyvinyl butyral, polyvinyl pyrrolidone and the like. Typically, this layer is of a thickness of less than about 0.6 micron.

Imaging members of the present invention exhibit excellent xerographic properties in embodiments thereof. For example, values for dark development potential ($V_{ddp}$) can range from about −400 to about −975. Preferred ranges for dark development potential for the imaging members of the present invention are usually about −400 to −900 volts with −800 volts being especially preferred in embodiments. High dark development potentials permit high contrast potentials, which result in images of high quality with essentially no background development.

The imaging members of the present invention in embodiments thereof also exhibit low dark decay values of, for example, about −50 volts per second or less. Low dark decay values can be of importance for developing high quality images since dark decay measures the amount of charge that disappears after charging of the photoreceptor, and a large difference in charge between exposed and unexposed areas of the photoreceptor results in images with high contrast. Acceptable values for dark decay vary depending on the design of the imaging apparatus in which the imaging members are contained. This dark decay may be as high as −100 volts per second with −50 volts, and −10 to −20 volts per second being preferred in embodiments.

Residual potential values ($V_R$) for the imaging members of the present invention in embodiments thereof are excellent, ranging from, for example, about −5 volts to about −50 volts. Residual potential is a measure of the amount of charge remaining on the imaging member after erasure by exposure to light and prior to imaging. Residual potentials of −5 to −15 are considered very exceptional.

Photosensitivity values ($E_{0.5ddp}$ at 600 nanometers) for the imaging members of the present invention in embodiments thereof are acceptable and, in some instances excellent, and can be, for example, from about 4 to about 25 ergs per square centimeter. Acceptable photosensitivity values vary depending on the design of the imaging apparatus in which the imaging members are contained; thus in some instances, values as high as 40 or 50 are acceptable, and values of about 5 can be preferred.

The present invention also encompasses a method of generating images with the photoconductive imaging members disclosed herein. The method comprises the steps of generating an electrostatic image on a photoconductive imaging member of the present invention, subsequently developing the electrostatic image with known developer compositions comprised of resin particles, pigment particles, additives, including charge control agents and carrier particles, reference U.S. Pat. No. 4,558,108; 4,560,535; 3,590,000; 4,264,672; 3,900,588 and 3,849,182, the disclosures of each of these patents being totally incorporated herein by reference, transferring the developed electrostatic image to a suitable substrate, and permanently affixing the transferred image to the substrate. Development of the image may be achieved by a number of methods, such as cascade, touchdown, powder cloud, magnetic brush, and the like. Transfer of the developed image to a substrate may be by any method, including those wherein a corotron or a biased roll is selected. The fixing step may be performed by means of any suitable method, such as flash fusing, heat fusing, pressure fusing, vapor fusing, and the like.

The imaging members of the present invention can be prepared by a number of different known processes such as those illustrated in the U.S. Pat. No. 4,886,722, the disclosure of which is totally incorporated herein by reference. In one process embodiment, the alkylalkoxy squaraine photogenerator is coated onto a supporting substrate with a Bird applicator, for example, followed by the solution coating of the charge transport layer, and thereafter drying in, for example, an oven.

Examples of supporting substrates, charge transport layers, and other layers that may be selected for the imaging members of the present invention are illustrated in U.S. Pat. No. 4,585,884; 4,584,253 and 4,563,408, the disclosures of which are totally incorporated herein by reference.

The following Examples are being supplied to further define various species of the present invention, it being noted that these Examples are intended to illustrate and not limit the scope of the present invention. Parts and percentages are by weight unless otherwise indicated.

EXAMPLE I 3-methyl-4-methoxyphenyl acetic acid, 7.15 grams, 40 millimoles, was reacted with an excess amount of thionyl chloride, 6 grams, 50 millimoles, in a 50 milliliter round bottom flask at 60° C. for 3 hours. The product mixture resulting was cooled to room temperature, about 25° C., and any excess thionyl chloride was removed with a water aspirator. Pure, about 99 percent purity, 3-methyl-4-methoxyyphenylacetyl chloride was isolated as a light reddish oil by vacuum distillation, yielding 5.82 grams, 73.3 percent yield. The boiling point of the aforementioned product was 115° C. at about 2 millimeters of mercury. IR (neat): 1,800 cm$^{-1}$ (C=O).

EXAMPLE II 1-(3′-methyl-4′-methoxyphenyl)-2-hydroxycyclobutene-3,4-dione was synthesized by a (2+2) cycloaddition reaction similar to that reported by Bellus J. Am. Chem. Soc., 100, 8026 (1978), the disclosure of which is totally incorporated herein by reference.

Tetraethoxyethylene, which was freshly synthesized using the procedure of Bellus et al. Helv. Chim. Acta., 63, 1130 (1980), the disclosure of which is totally incorporated herein by reference, (4 grams, 19.5 millimoles), triethylamine (2.95 grams), and n-hexane (60 milliliters) were discharged in a 300 milliliter three-neck flask which was equipped with a mechanical stirrer and a nitrogen inlet. There was then added dropwise to the aforementioned n-hexane solution over a two hour period an ether solution in 2 milliliters of diethylether containing 5.8 grams of 3-methyl-4-methoxyphenylacetyl chloride. A yellow precipitate was formed during the addition of the acid chloride. After the addition was completed, the resulting mixture was stirred at room temperature, overnight, about 18 hours, followed by filtration. The yellow cake obtained was washed with ether (3×100 milliliters), and the filtrates were combined. After removing the solvent (the filtrate is comprised of a mixture of hexane and ether) under reduced pressure on a rotatory evaporator, 8.2 grams of an orange-yellow residue were obtained. This residue was then hydrolyzed at reflux at an oil bath temperature of about 110° C. with 40 milliliters, 18 percent, of hydrochloric for 4 hours. The product was then isolated by filtration. After recrystallization from a mixture of toluene and acetone, a 2:1 ratio, a light yellow solid which was subsequently identified as 1-(3′-methyl-4′-methoxyphenyl)-2-hydroxycyclobutene-3,4-dione was obtained in a yield of 1.28 grams, 30 percent. The melting point of the aforementioned product was about 250° C. IR (KBr): 1,712 and 1,790 cm$^{-1}$, $^1$H NMR (DMSO-d$_6$): δ

2.19 (s, 3H), 3.85 (s, 3H), 7.07 (d, J=8.5 Hz, 1H), 7.81 (s, 1H) and and 7.87 (AB$_q$, J$_A$=8.5 Hz, J$_B$=1.5 Hz, 1H). Analysis calculated for the above product $C_{12}H_{10}O_4$: C-66.05, H-4.62; Found: C-66.11, H-4.59.

EXAMPLE III

The 1-(3'-methyl-4'-methoxyphenyl)-2-hydroxycyclobutene-3,4-dione obtained from Example II, 0.95 gram, 4.35 millimoles, 3-fluoro-N,N-dimethylaniline, 0.65 gram, 4.7 millimoles, tributyl orthoformate, 3.3 milliliters, and 35 milliliters of 2-propanol were placed in a 100 milliliter 3-neck flask, which was equipped with a magnetic stirrer and a nitrogen inlet. The resulting mixture was stirred and heated to reflux at an oil bath temperature of about 100° c. for 1.5 hours. After cooling to about 0° to 5° C., the precipitated product was isolated by filtration, and the solid product was purified by washing with 2-propanol until the filtrate was light blue, in color, followed by rinsing with a small quantity of ether, about 5 milliliters. Thereafter, the mixture was vacuum dried, yielding 0.60 gram, 41 percent yield, of a light blue solid powder, which was subsequently identified by elemental analysis, and IR as 3-methyl-4-methoxyphenyl-2'-fluoro-4'-dimethylaminophenyl squaraine with a melting point of 224° to 226° C.; IR (KBr): 1,596 cm$^{-1}$ (squaraine). Analysis calculated for the above product $C_{20}H_{18}NO_3F$: C-70.78, H-5.35, N-4.13 and F-5.60; Found: C-70.90, H-5.62, N-3.87 and F-4.95.

EXAMPLE IV

There was prepared a photoresponsive device containing as the photoconductive material the squaraine as prepared in accordance with Example III, and as a hole transport layer an aryl amine dispersed in a resinous binder. To a 1 ounce amber bottle were added 52.8 milligrams of polyvinyl formal (obtained from Scientific Polymer Products, Inc., formal content 82 percent, acetate content 12 percent, hydroxy content 6 percent) and 10 milliliters of methylene chloride. To the bottle were then added 211.2 milligrams of the above squaraine pigment, 3-methyl-4-methoxyphenyl-2'-fluoro-4'-dimethylaminophenyl squaraine, and about 90 grams of steel shot (⅛ inch diameter, number 302 stainless steel shot). The bottle was then placed on a Red Devil Paint Conditioner (Model 5100X) and shaken for about 2 hours. The resulting dispersion was coated onto a 7.5 inch by 10 inch brush-grained aluminum substrate obtained from Ron Ink Company using a Gardner Mechanical Drive with a 6 inch wide Bird Film Applicator (0.5 mil wet gap) inside a humidity controlled glove box. The relative humidity of the glove box was controlled by dry air to about 25 percent, or less. The resulting photogenerator layer was air dried for about 30 minutes and then vacuum dried for about 1 hour at 100° C. before any further coating. The thickness of the charge generator layer was about 0.5 micron as estimated from TEM micrographs.

The above charge photogenerator layer was overcoated with a hole transport layer comprised of 60 weight percent of the polycarbonate MAKROLON ® obtained from Larkensabricken Bayer AG, and 40 percent of aryl diamine hole transport molecules prepared as follows. A solution containing 4.2 grams of MAKROLON ®, a polycarbonate resin obtained from Larkensabricken Bayer A. G., and 2.8 grams of N,N'-bis(-3''-methylphenyl)-1,1'-biphenyl-4,4'-diamine prepared as disclosed in U.S. Pat. No. 4,265,990, the disclosure of which is totally incorporated herein by reference, was prepared by dissolving the above materials in 31 milliliters of methylene chloride inside a 2 ounce amber bottle. The transport layer was obtained by coating the aforementioned solution onto the above squaraine charge generator layer using a 3.5 inch wide, 5 mil wet gap Bird Film Applicator, resulting in a transport layer about 27 microns thick. The resulting photoconductive device was air dried for about 1 hour and vacuum dried at 100° C. for about 16 hours before evaluation on a flat plate imaging test fixture.

More specifically, the imaging member prepared was evaluated as follows. Xerographic measurements were made on a flat plate scanner using 2 inch by 2.5 inch samples of the above prepared imaging member. The surface potential of the device was monitored with a capacitively coupled ring probe connected to a Keithley electrometer (Model 610C) in the Coulomb mode. The output of the electrometer was displayed on a strip-chart recorder (HP Model 740A) which was calibrated by applying known voltage on an uncoated aluminum substrate. The exposure wavelength and the intensity were selected and adjusted using interference and neutral density filters, respectively. With the shutter closed, the dark decay was measured. With the shutter open, the photosensitivity at a known light exposure was recorded. The imaging member was charged to about −1,000 volts at the peak voltage and was allowed to discharge in the dark for 2 to 3 seconds to determine the dark decay. Subsequently, the imaging member was exposed to an erase lamp to photodischarge the surface charge and to determine its residual voltage ($V_R$). Thereafter, the imaging member was charged in a similar manner and exposed to monochromatic radiation at the dark development potential, and the sensitivity of the member was determined in terms of $E_{\frac{1}{2}}$, which represents the energy required to discharge half of the dark development potential. The imaging member exhibited a maximum charge acceptance in volts of greater than 1,000 volts, a dark development potential ($V_{ddp}$) of −970 volts, a dark decay of −20 volts per second, an $E_{0.5ddp}$, the energy to discharge half the potential at 450 nanometers (erg/cm$^2$) of 12.4, an $E_{0.5ddp}$, the energy to discharge half the potential at 520 nanometers (erg/cm$^2$) of 11, an $E_{0.5ddp}$, the energy to discharge half the potential at 650 nanometers (erg/cm$^2$) of 9.9, an $E_{0.5ddp}$, the energy to discharge half the potential at 700 nanometers (erg/cm$^2$) of 8.4, an $E_{0.5ddp}$, the energy to discharge half the potential at 750 nanometers (erg/cm$^2$) of 6.9, an $E_{0.5ddp}$, the energy to discharge half the potential at 790 nanometers (erg/cm$^2$) of 9.1, and an $E_{0.5ddp}$, the energy to discharge half the potential at 800 nanometers (erg/cm$^2$) of 10.9.

The above photoreceptor device can be incorporated into a xerographic imaging test fixture and subsequent to development of the formed latent images with a toner comprised of 88 percent by weight of styrene n-butyl methacrylate (58/42) resin particles, 10 percent by weight of carbon black, and 2 percent by weight of the charge additive distearyl dimethyl ammonium methyl sulfate, copies of excellent resolution and high quality may be obtained.

EXAMPLE V

A photoconductive imaging member was prepared by repeating the procedure of Example IV with the exceptions that there was selected polycarbonate PC (Z) in place of MAKROLON ®, and toluene in place of methylene chloride as the coating solvent for the aryl amine hole transport layer. The imaging member exhibited a maximum charge acceptance in volts of about −1,000 volts, a dark development potential ($V_{ddp}$) of −980 volts, a dark decay of −14 volts per second, an $E_{0.5ddp}$, the energy to discharge half the potential at 450 nanometers (erg/cm$^2$) of 25.4, an $E_{0.5ddp}$, the energy to discharge half the potential at 520 nanometers (erg/cm$^2$) of 20.9, an $E_{0.5ddp}$, the energy to discharge half the potential at 600 nanometers (erg/cm$^2$) of 17.6, an $E_{0.5ddp}$, the energy to discharge half the potential at 650 nanometers (erg/cm$^2$) of 21.0, an $E_{0.5ddp}$, the energy to discharge half the potential at 700 nanometers (erg/cm$^2$) of 18.1, an $E_{0.5ddp}$, the energy to discharge half the potential at 750 nanometers (erg/cm$^2$) of 13.8; an $E_{0.5ddp}$, the energy to discharge half the potential at 760 nanometers (erg/cm$^2$) of 16.5; an $E_{0.5ddp}$, the energy to discharge half the potential at 790 nanometers (erg/cm$^2$) of 13.0; and an $E_{0.5ddp}$, the energy to discharge half the potential at 800 nanometers (erg/cm$^2$) of 17.3.

Other modifications of the present invention will occur to those skilled in the art subsequent to a review of the present application. These modifications, and equivalents thereof are intended to be included within the scope of this invention.

What is claimed is:

1. A photoconductive imaging member consisting essentially of a supporting substrate, a photogenerating layer of an alkoxy squaraine selected from the group consisting of 3-methyl-4-methoxyphenyl-2'-fluoro-4'-dimethylaminophenyl squaraine; 3-methyl-4-methoxyphenyl-4'-dimethylaminophenyl squaraine; 3-methyl-4-methoxyphenyl-2'-methyl-4'-dimethylaminophenyl squaraine; 3-methyl-4-methoxyphenyl-2'-hydroxy-4'-dimethylaminophenyl squaraine; 3-methyl-4-methoxyphenyl-2'-methoxy-4'-dimethylaminophenyl squaraine; 3-methyl-4-methoxyphenyl-2'-chloro-4'-dimethylaminophenyl squaraine; 3-methyl-4-methoxyphenyl-2',6'difluoro-4'-dimethylaminophenyl squaraine; 3-methyl-4-methoxyphenyl-2'fluoro-4'-N-pyrrolidinophenyl squaraine; 3-methyl-4-methoxyphenyl-2'fluoro-4'-benzylmethylaminophenyl squarine; and 3-methyl-4-methoxyphenyl-8'-fluoro-9'-julolidinyl squarine; and a charge transport layer.

2. A photoconductive imaging member in accordance with claim 1 wherein the photogenerating layer is situated between the supporting substrate and the charge transport layer.

3. A photoconductive imaging member in accordance with claim 1 wherein the transport layer is situated between the supporting substrate and the photogenerating layer.

4. A photoconductive imaging member in accordance with claim 1 wherein the photoconductive imaging member includes a metal oxide hole blocking layer situated between the supporting substrate and the photogenerating layer.

5. A photoconductive imaging member in accordance with claim 4 wherein the metal oxide is aluminum oxide.

6. A photoconductive imaging member in accordance with claim 4 wherein the metal oxide hole blocking layer has a thickness of less than about 500 Angstroms.

7. A photoconductive imaging member in accordance with claim 4 wherein the photoconductive imaging member contains an adhesive interface layer situated between the supporting substrate and the metal oxide hole blocking layer.

8. A photoconductive imaging member in accordance with claim 7 wherein the adhesive interface layer comprises a polymeric material selected from the group consisting of polyester, polyvinylbutyral, and polyvinyl pyrrolidone.

9. A photoconductive imaging member in accordance with claim 7 wherein the adhesive interface layer has a thickness of less than about 0.6 micron.

10. A photoconductive imaging member in accordance with claim 1 wherein the supporting substrate is a metal.

11. A photoconductive imaging member in accordance with claim 10 wherein the metal is aluminum or titanium.

12. A photoconductive imaging member in accordance with claim 1 wherein the supporting substrate is an organic polymeric composition.

13. A photoconductive imaging member in accordance with claim 1 wherein the supporting substrate has a thickness of from about 3 to about 100 mils.

14. A photoconductive imaging member in accordance with claim 1 wherein the alkoxy squaraine layer has a thickness of from about 0.05 to about 10 microns.

15. A photoconductive imaging member in accordance with claim 1 wherein the charge transport layer has a thickness of from about 5 to about 50 microns.

16. A photoconductive imaging member in accordance with claim 1 wherein the alkoxy squaraine compound is dispersed in a resinous binder in an amount of from about 5 percent by weight to about 95 percent by weight.

17. A photoconductive imaging member in accordance with claim 16 wherein the resinous binder is a polyester, polyvinyl butyral, a polycarbonate, polyvinyl carbazole or polyvinyl formal.

18. A photoconductive imaging member in accordance with claim 1 wherein the charge transport layer comprises an aryl amine compound dispersed in a highly insulating and transparent organic resinous binder.

19. A photoconductive imaging member in accordance with claim 18 wherein the resinous binder is a polyester, a polyvinyl butyral, a polycarbonate, or a polyvinyl formal.

20. A method of imaging which comprises the steps of:
   (a) generating an electrostatic image on the photoconductive imaging member of claim 1,
   (b) subsequently developing the electrostatic image;
   (c) transferring the developed electrostatic image to a suitable substrate; and
   (d) permanently affixing the transferred image to the substrate.

21. A photoconductive imaging member consisting essentially of a hole transport layer, and a photogenerating layer comprised of an alkoxy squaraine selected from the group consisting of 3-methyl-4-methoxyphenyl-2'-fluoro-4'-dimethylaminophenyl squaraine; 3-methyl-4-methoxyphenyl-4'-dimethylaminophenyl squaraine; 3-methyl-4-methoxyphenyl-2'-methyl-4'-dimethylaminophenyl squaraine; 3-methyl-4-methoxyphenyl-2'-hydroxy-4'-dimethylaminophenyl squaraine; 3-methyl-4-methoxyphenyl-2'-methoxy-4'-dimethylaminophenyl squaraine; 3-methyl-4-methoxyphenyl-2'-chloro-4'-dimethylaminophenyl squaraine; 3-methyl-4-methoxyphenyl-2',6'difluoro-4'-dimethylaminophenyl squaraine; 3-methyl-4-methoxyphenyl-2'fluoro-4'-N-pyrrolidinophenyl squaraine; 3-methyl-4-methoxyphenyl-2'fluoro-4'-benzylmethylaminophenylsquaraine; and 3-methyl-4-methoxyphenyl-8'-fluoro-9'-julolidinyl squaraine.

22. A photoconductive imaging member in accordance with claim 21 further including a supporting substrate.

23. A photoconductive imaging member in accordance with claim 1 wherein the photogenerating layer is of a thickness in the range of from about 0.05 to about 10 microns and is comprised of 3-methyl-4-methoxyphenyl-2'-fluoro-4'-dimethylaminophenyl squaraine.

* * * * *